United States Patent
Spero et al.

(10) Patent No.: US 7,266,994 B1
(45) Date of Patent: Sep. 11, 2007

(54) MEASURING PARTICULATE IN LIQUID STORAGE TANKS

(75) Inventors: Daniel Spero, New Riegel, OH (US); James Sheridan, Ironton, OH (US)

(73) Assignee: Marathon Ashland Petroleum Co., Findlay, OH (US)

( * ) Notice: Subject to any disclaimer, the term of this patent is extended or adjusted under 35 U.S.C. 154(b) by 410 days.

(21) Appl. No.: 10/960,475

(22) Filed: Oct. 6, 2004

Related U.S. Application Data

(60) Provisional application No. 60/519,816, filed on Nov. 12, 2003.

(51) Int. Cl.
G01N 15/06 (2006.01)
G01N 21/00 (2006.01)
B42D 15/00 (2006.01)

(52) U.S. Cl. .............. 73/61.71; 356/239.5; 356/239.6; 283/115

(58) Field of Classification Search ............... 73/61.71, 73/53.01; 283/115; 116/334; 356/239.5, 356/239.6
See application file for complete search history.

(56) References Cited

U.S. PATENT DOCUMENTS

| | | | | |
|---|---|---|---|---|
| 377,086 | A * | 1/1888 | Schroeder | 434/98 |
| 935,474 | A * | 9/1909 | Eckart | 434/98 |
| 1,598,899 | A * | 9/1926 | Vogel | 434/98 |
| 2,380,244 | A * | 7/1945 | Jones et al. | 396/563 |
| RE31,232 | E * | 5/1983 | Butera | 73/23.33 |
| 4,523,852 | A * | 6/1985 | Bauer | 356/421 |
| 4,527,895 | A * | 7/1985 | Rubin | 356/30 |
| 4,575,124 | A * | 3/1986 | Morrison | 283/115 |
| 4,588,298 | A * | 5/1986 | Nakamura | 356/443 |
| 5,056,826 | A * | 10/1991 | Suwa | 283/67 |
| 5,313,824 | A * | 5/1994 | Herguth et al. | 73/53.05 |
| 5,534,952 | A * | 7/1996 | Zanecchia et al. | 351/200 |
| 5,710,373 | A * | 1/1998 | Osmanski | 73/53.05 |
| 5,917,987 | A * | 6/1999 | Neyman | 386/42 |
| 6,598,464 | B1 * | 7/2003 | Rossi | 73/53.05 |
| 6,734,973 | B1 * | 5/2004 | Mutters et al. | 356/421 |
| 6,829,850 | B2 * | 12/2004 | Goode | 40/124.01 |
| 6,982,108 | B2 * | 1/2006 | Janssen et al. | 428/42.1 |

FOREIGN PATENT DOCUMENTS

JP 11064954 * 3/1999

OTHER PUBLICATIONS

"Grading Canadian Coins", http://web.archive.org/web/20030623220025/http://www.coinoisseur.com/GradingCoins.html, last modified on Jun. 17, 2003.*

ASTM E 125-63, Standard Reference Photographs for Magnetic Particle Indications on Ferrous Castings, reapproved 1997.*

Alan D. Hewitt, "Evaluation of H.E.L.P. Mate 2000 for the Identification and Quantification of Petroleum Hydrocarbon Products", US Army Corps of Engineers Engineer Research and Development Center, Technical Report ERDC/CRREL-TR-00-20 Sep. 2000.*

* cited by examiner

*Primary Examiner*—Michael Cygan
(74) *Attorney, Agent, or Firm*—Emch, Schaffer, Schaub & Porcello, Co., L.P.A.

(57) ABSTRACT

This device provides for measuring the particulate content in a fluid storage tank. A sample of fluid is taken from a fluid storage tank; and compared to a field visual reference chart. Using this chart results in identifying tanks containing a maximum or average particulate allowable.

17 Claims, 1 Drawing Sheet
(1 of 1 Drawing Sheet(s) Filed in Color)

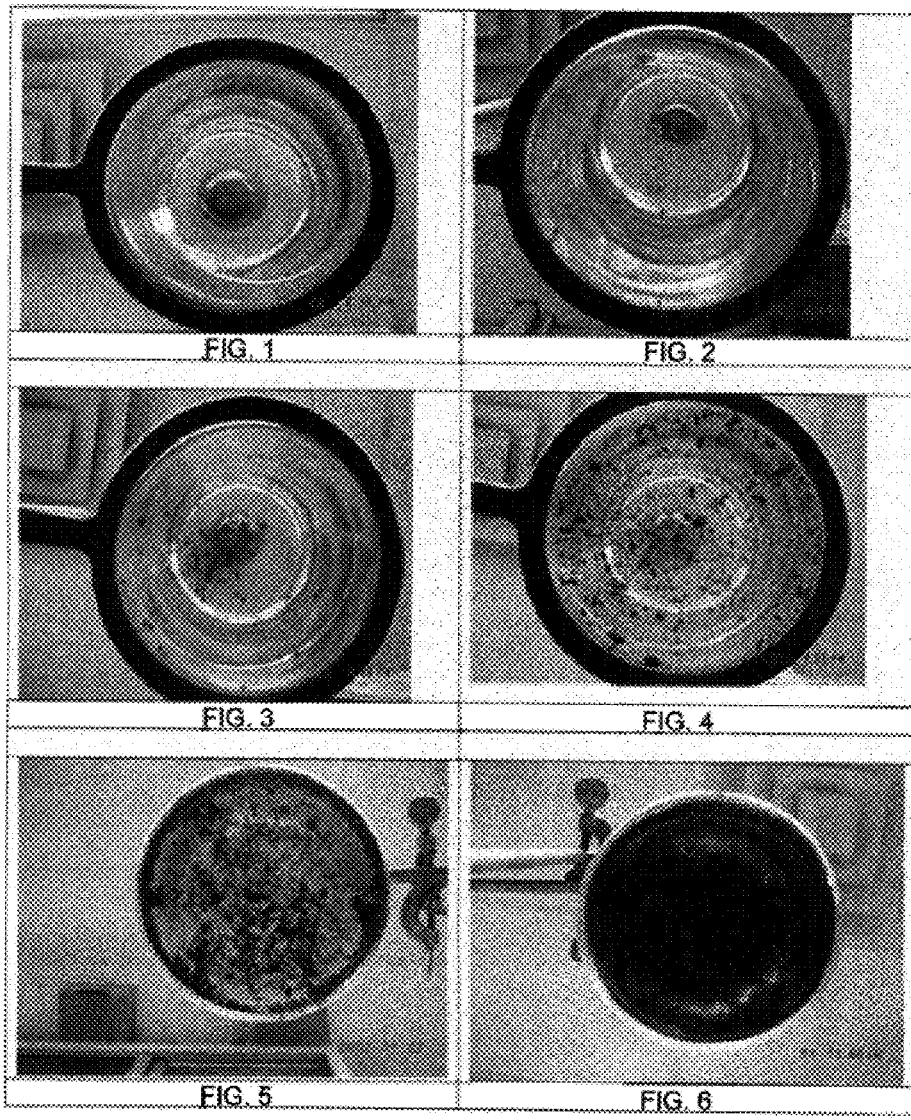
Field Visual Reference Chart

MEASURING PARTICULATE IN LIQUID STORAGE TANKS

CROSS REFERENCE TO RELATED APPLICATION

This patent application is a conversion of provisional patent application Ser. No. 60/519,816 filed Nov. 12, 2003.

TECHNICAL FIELD

This invention relates to a method and apparatus for measuring the amount of particulate in liquid storage tanks. In the preferred embodiment, rust particulate in fuel storage tanks is analyzed in comparison with a field reference chart.

BACKGROUND OF THE INVENTION

Large storage tanks are used to store a variety of liquids, including petroleum, and various petroleum products. Commonly these tanks are subject to corrosion and eventual failure over time. Particulate and sediment will almost always be present in such storage tanks necessitating frequent inspections to ensure quality of the product stored in the tank. Such regular inspections can be expensive and inconvenient, especially if it is necessary to empty a tank each time it is to be inspected. Also complicating the inspection process is the concern for the safety of the inspector.

Older systems for measuring basic particulate and water contamination are time consuming and inaccurate. One system includes the steps of removing a sample, heating the sample and centrifuging the sample to separate particulate, water and petroleum products. This system requires too much handling and processing and usually involves the shipment of samples to a lab for analysis.

More recent systems for monitoring particulate matter require complicated, expensive equipment. One system uses a back scattered laser with detection optics. Another system for in situ measurement of corrosion in filled tanks uses ultrasonic pulses with an ultrasonic transducer in combination with a remote, automated device inside the tank. Another system for in-line particulate monitoring uses a controller with a series of in-line accumulators and sampling units.

A need exists for a simple, reliable tank inspection and sampling program.

BRIEF SUMMARY OF THE INVENTION

The present invention is directed to a method and apparatus for measuring the particulate content in a fluid storage tank. A particulate reference chart showing containers of fluid with varying amounts of particulate contamination is used by field operators to usually analyze contaminant concentration in samples retrieved from storage tanks. A sample of fluid taken from a fluid storage tank and compared to the field visual reference chart. Once armed with the reference chart, industry professionals can easily inspect tank samples and compare them to the reference chart. Using this chart results in quick and reliable testing, leading to quick decision making regarding the quality of the storage tanks and its contained fluid Other objects and advantages of the present invention will become, apparent to those skilled in the art upon a review of the following detailed description of the preferred embodiments and the accompanying drawings.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

FIGS. 1–6 show field visual reference charts. The figures are digital pictures of varying levels of particulate in quart samples of gasoline. UST as used herein means underground storage tank.

FIG. 1 is clear and bright, i.e. gasoline with no particulate.

FIG. 2 shows the maximum particulate allowable for consumer sales.

FIG. 3 shows the average particulate found in a distribution system.

FIG. 4 shows the maximum particulate allowable in a distribution system.

FIG. 5 shows the average particulate found in a consumer UST.

FIG. 6 shows the maximum allowable particulate in a consumer UST.

DETAILED DESCRIPTION OF THE INVENTION

The base point of the tank inspection program of this invention is the amount of rust and particulate present in a one liter sample when the particulate measured 50 mg per liter. Once armed with the reference chart, industry professionals could easily inspect tank samples and compare them to the reference chart. Using this chart results in quick and reliable sample results and reduced costs in shipping samples.

The field visual reference chart of this invention provides a working knowledge of the amount of particulate found in gasoline and diesel petroleum tanks. The charts show how much or how little particulate was being found during sampling procedures. Specific guidelines were set on the procedures used to obtain the samples. The charts provide a certainty that the samples properly represent the tank bottoms. The chart easily categorizes the samples into groups in case further action is required. Using a visual chart is the best tool.

FIG. 1 shows a digital picture of a sample containing virtually no particulate, i.e., clear and bright gasoline.

FIG. 2 is a digital picture of a one liter sample of gasoline showing the maximum particulate allowable for consumer sales.

FIG. 3 is a digital picture of a one liter sample of gasoline having a particulate content which is the average particulate found in a distribution system.

FIG. 4 is a digital picture of a one liter sample of gasoline having a particulate content showing the maximum particulate allowable in a distribution system.

FIG. 5 is a digital picture of a one liter sample of gasoline having a particulate content showing the average particulate found in a consumer UST.

FIG. 6 is a digital picture of a one liter sample of gasoline having a particulate content showing the maximum particulate allowable in a consumer UST.

Charts may be developed for underground storage tanks as well as above ground tanks. The chart may be used throughout the storage tank clean-up process. Sampling procedures and reference chart determine how much particulate resides in the bottoms of underground and above ground storage tanks. They may indicate when a tank needs to be cleaned or replaced.

In the preferred embodiment the storage tanks are organic chemical liquid storage tanks such as hydrocarbon fuel storage tanks. The method and apparatus especially were designed for gasoline storage tanks. In the preferred embodiment, the measure is an amount of particulate in the liquid. More preferably, the measure is the amount of particulate in tank bottom samples. The samples range from a liquid having no amount of particulate therein to a liquid saturated with the particulate. A liquid having no particulate is clear and a liquid saturated with particulate has a dark color.

The step of comparing is a visual step. The visual step of comparing provides a sampling and inspection protocol for assessing storage tank particulate.

As used herein, the terms "organic chemical liquid" and "organic chemical liquids" are taken to refer broadly or generally to a liquid or liquids, respectively, of compounds (and mixtures thereof) based on carbon, principally having chains or rings and also containing hydrogen, with or without an oxygen, nitrogen, or other elements. Accordingly, the invention is seen to have wide applicability in materials handled as refinery or chemical plant products, or other operations or sources which have water vapor condensation problems. Thus, while a preferred embodiment of the invention is for refined products, such as gasoline range materials and distillates are equally applicable as well as distillates such as fuel oil, and hydrocarbons such as benzene, ethanol, or methanol.

Samples were obtained from underground storage tanks. The samples were collected, labeled and photographed.

The measuring is carried out using the following guidelines:

Fill in the complete site information at the top of the report.

Tanks & Tank Bottom Samplings:

Identify the unleaded grades of gasoline for each tank.

Stick and record water levels for each tank in inches of water regardless of filter inspection results.

Take tank bottom samples only if: particulate visible on that tank's respective dispenser filter; or no filters were originally on dispensers prior to inspections.

Drain tank bottom sample and pour into clear glass sampling jar.

Visually inspect sample for particulate. Denote on inspection report if the sample is clear (no particulate), light (some particulate) or heavy (bottom of sampling jar is coated with particulate). Compare the samples to the Field Visual Reference Chart.

Pour all tank bottom samples back into the tank from which the sample was taken. If sample is clear, the sampling jar may be reused. If the sample contains particulate (light or heavy), do not reuse jar.

Tank Bottom Samplings:

Identify the unleaded grades of gasoline for each tank.

Stick and record water levels for each tank in inches of water.

Take samples of each gasoline product tank at both the fill end and the opposite end of the tank using a bacon bomb sample unit. Note: It may be necessary to pull the submersible pump in order to take a sample at the opposite end of the tank. Drain tank bottom samples and pour into clear glass sampling jar. Visually inspect sample for particulate. Compare the samples with the "Field Visual Reference Chart" to determine the amount of particulate present and record the figure number which best describes the sample.

Determine the particulate level at the fill end of a tank best represented by the "Field Visual Reference Chart".

Return sample to tank. If the sample contained particulates do not reuse the jar.

Complete the inspection report. This report records the actual raw data of the visual field inspection.

The predetermined samples represent a range of particulate. Clear represents no particulate. Light represents some particulate and heavy (dark) represents substantial particulate.

Visually inspect sample for particulate. Denote on inspection report if the sample is clear (no particulate), light (some particulate) or heavy (bottom of sampling jar is coated with particulate).

In addition to these embodiments, persons skilled in the art can see that numerous modifications and changes may be made to the above invention without departing from the intended spirit and scope thereof.

I claim:

1. A visual apparatus for measuring particulate content in a gasoline or diesel fuel storage tank using a field visual reference comprising:

a sample of gasoline or diesel fuel taken from a gasoline or diesel fuel storage tank;

a photograph image of a first sample consisting of only gasoline or diesel fuel;

a photograph image of a second sample of gasoline or diesel fuel containing a maximum allowable particulate for consumer sales; and a multiplicity of photograph images of samples of gasoline or diesel fuel, each sample of the multiplicity containing a different, measured amount of particulate, wherein the particulate has settled to the bottom of the sample.

2. An apparatus according to claim 1 wherein the particulate is rust.

3. An apparatus according to claim 1 wherein the particulate is solid material.

4. An apparatus according to claim 1 wherein one of the photograph images represents a sample containing 50 mg of the particulate per liter of gasoline or diesel fuel.

5. An apparatus according to claim 1 wherein one of the photograph images represents a sample showing a maximum particulate allowable for a distribution system.

6. An apparatus according to claim 1 wherein one of the photograph images represents a sample showing a maximum particulate allowable for an underground storage tank.

7. An apparatus according to claim 1 wherein the storage tank is an underground tank.

8. An apparatus according to claim 1 wherein the storage tank is a steel tank.

9. An apparatus according to claim 1 wherein the photograph images are digital photographs.

10. A visual method for measuring particulate content in a gasoline or diesel fuel storage tank using a field visual reference comprising the steps of:

providing a sample of gasoline or diesel fuel taken from a gasoline or diesel fuel storage tank;

providing a photograph image of a first sample consisting of only gasoline or diesel fuel;

providing a photograph image of a second sample of gasoline or diesel fuel containing a maximum allowable particulate for consumer sales;

a multiplicity of photograph images of sample gasoline or diesel fuel, each sample of the multiplicity containing a different, measured amount of particulate;

settling the particulate to the bottom of the sample;

visually comparing the sample of gasoline or diesel fuel from the storage tank to photograph images; and making a decision on the quality of the gasoline or diesel fuel in the storage tank based on the visually comparing.

11. A method according to claim 10 including the step of providing one image of a container containing 50 mg of the particulate per liter of the fluid.

12. A method according to claim 10 including the step of providing one image of a sample containing a maximum particulate allowable for a distribution system.

13. A method according to claim 10 including the step of providing one image of a sample containing a maximum particulate allowable for an underground storage tank.

14. A method according to claim 10 wherein the storage tank is an underground tank.

15. A method according to claim 10 wherein the storage tank is a steel tank.

16. A method according to claim 10 wherein the particulate is rust.

17. A method according to claim 10 wherein the particulate is solid material.

* * * * *